(12) United States Patent
Ganesan et al.

(10) Patent No.: US 7,615,672 B2
(45) Date of Patent: Nov. 10, 2009

(54) PROCESS FOR THE PREPARATION OF N-HENEICOSANE

(75) Inventors: Kumaran Ganesan, Madhya Pradesh (IN); Ramesh Chandra Malhotra, Madhya Pradesh (IN); Ambati Narasimha Rao, Madhya Pradesh (IN); Pradeep Kumar Gupta, Madhya Pradesh (IN); Asheesh Kumar Jain, Madhya Pradesh (IN); Shri Prakash, Madhya Pradesh (IN); Krishnamurthy Sekhar, Madhya Pradesh (IN)

(73) Assignee: Defence Research & Development Organisation, New Delhi (IN)

( * ) Notice: Subject to any disclaimer, the term of this patent is extended or adjusted under 35 U.S.C. 154(b) by 52 days.

(21) Appl. No.: 11/883,155

(22) PCT Filed: Jun. 23, 2005

(86) PCT No.: PCT/IN2005/000213

§ 371 (c)(1),
(2), (4) Date: Apr. 8, 2008

(87) PCT Pub. No.: WO2006/090411

PCT Pub. Date: Aug. 31, 2006

(65) Prior Publication Data

US 2008/0293992 A1    Nov. 27, 2008

(30) Foreign Application Priority Data

Feb. 25, 2005  (IN) .......................... 418/DEL/2005

(51) Int. Cl.
  *C07C 1/207* (2006.01)
(52) U.S. Cl. ...................................... 585/310; 585/733
(58) Field of Classification Search ................ 585/310, 585/733
  See application file for complete search history.

(56) References Cited

U.S. PATENT DOCUMENTS 4,070,410 A    1/1978    Matishev et al.

OTHER PUBLICATIONS

Muller, A., et al. "Further X-Ray Measurements on Longchain Compounds (n-Hydrocarbons)." J. Chem. Soc. (1925) pp. 599-600.
Oyamada, T. "Synthesis of 4-hydroxy-3-methoxyphenylethyl heptadecyl and nonadecyl ketones and and of 4-hydroxy-3-methoxystyryl . . ."Database Caplus 'Online! Chem. Abstracts Service and Science Repts. Tohoku Imp. Univ., 1st Ser. 18 (1929) pp. 625-637 XP002356197.

*Primary Examiner*—Thuan Dinh Dang
(74) *Attorney, Agent, or Firm*—Ladas and Parry LLP

(57) ABSTRACT

A process for the preparation of n-heneicosane is disclosed. The process comprises (a) reacting 2,4-alkanedione with 1-bromooctadecane in absolute ethanol in the presence of 18-crown-6 as catalyst to produce 2-heneicosanone; and (b) reducing said 2-heneicosanone using hydrazine hydrate and potassium hydroxide in ethylene glycol to obtain n-heneicosane.

22 Claims, No Drawings

PROCESS FOR THE PREPARATION OF N-HENEICOSANE

FIELD OF INVENTION

This invention relates to a new process for the preparation of n-heneicosane, a straight-chain hydrocarbon.

PRIOR ART

Mosquitoes are medically the most important vectors, both in number of diseases they transmit and the magnitude of health problems these diseases cause world-wide. Various mosquito control methods are used to reduce or eliminate the spread of these vector-borne diseases. However, numerous environment problems exist with these mosquito control methods using various insecticides. Sometime by repeated spraying of insecticides, mosquitoes become insecticide-resistant. Control methods based on mosquito attractant chemicals (semiochemicals) have been attempted during the last two decades [U.S. Pat. No. 4,803,289 (1989); U.S. Pat. No. 4,844,892 (1989); U.S. Pat. No. 4,902,504 (1990); U.S. Pat. No. 4,907,366 (1990); U.S. Pat. No. 5,123,201 (1992); U.S. Pat. No. 5,165,926 (1992); U.S. Pat. No. 5,175,175 (1992); U.S. Pat. No. 6,267,953 (2001)]. These semiochemicals (pheromones or kairomones) include carbon dioxide gas, L-lactic acid, 1-octen-3-ol, dimethyl disulfide, dibutyl succinate, 2-undecyl acetate, etc. and are required in very small quantities than the traditional insecticides. However, the activities of these attractants are often inconsistent and below 50% attraction response in laboratory experiments.

A new approach to control mosquito breeding involves the use of oviposition attractant pheromone. Mosquitoes breed in marked oviposition sites (egg laying places) in aquatic habitats containing immature stages. The first oviposition attractant pheromone was isolated and identified as erythro-6-acetoxy-5-hexadecanolide (J. Chem. Soc., Chem. Commun. 59-60, 1982) in malaria transmitting mosquito, *Culex pipiens fatigans*. Later, the existence of similar pheromones in different mosquito species was investigated. Recently, n-heneicosane has been identified as an oviposition attractant pheromone of dengue transmitting mosquito, *Aedes aegypti* [Current Science, 78(11), 1295-96, 2000]. Since n-heneicosane attracts *Aedes aegypti* mosquitoes at concentrations less than 100 ppm level, it is used in attracticide formulations to develop new environment and eco-friendly mosquito control strategies.

In addition, n-neneicosane is also reported as pheromone component in few insects (Pherolist database). Thus it will find application to develop pheromone based control methods for these insects also.

n-Heneicosane (CAS no. 629-94-7) is a saturated straight-chain hydrocarbon having molecular formula $C_{21}H_{44}$ and molecular weight of 296. It is a white waxy solid having melting point 40° C. It is also used in analytical chemistry as a standard and for retention indices studies. In spite of the various applications of n-heneicosane, there is no simple, cost-effective synthetic method available for its preparation and upscaling to manufacturing scale till now. Therefore, a process for the synthesis of n-heneicosane from commercially available raw materials is a long-felt requirement and the present invention satisfies this need.

One of the general processes known in the art for the preparation of n-heneicosane involves fractional distillation of petroleum constitutent containing long-chain alkanes ($C_{20}$ to $C_{34}$) as referred in all the organic chemistry text books.

The main disadvantage of this technology is that the above process is very tedious as it involves separation of pure n-heneicosane by fractional distillation from the mixture of close boiling hydrocarbons.

Still another disadvantage of this technology is that the composition of raw material varies with source of petroleum well.

Another disadvantage of this technology is that the process is not cost effective.

Another known process in the art for preparation of n-heneicosane involves the following five steps (Rec trav chim., 55, 903-914, 1936, Chemical Abstract 31, 1937, 1000):

(i) preparation of n-undecanoic acid by the hydrogenation of undecylenic acid in acetic acid in the presence of platinum black as catalyst.

(ii) preparation of ethyl undecanoate by the reaction of n-undecanoic acid with ethyl alcohol using sulphuric acid as catalyst;

(iii) self-condensation of ethyl undecanoate in presence of active sodium ethoxide at 120° C. under vacuum to give 2-Nonyl-3-oxo-tridecanoic acid ethyl ester (a β-keto ester);

(iv) saponification of the β-keto ester to give 11-heneicosanone; and (v) reduction of 11-heneicosanone with concentrated hydrochloric acid and zinc amalgam (Clemmensen reduction) to give n-heneicosane.

The major drawback of this method is that the process is not suitable for upscaling.

Another drawback of this method is that the products obtained in every step require purification either by distillation or crystallization. Hence, the overall yield of the final product is very low (8%).

Still another drawback of this method is that the process involves the use of sodium ethoxide in step (ii), which is moisture sensitive. Therefore, great caution should be employed in storage, handling and transfer operations.

Yet, another drawback of this method is that along with 2-Nonyl-3-oxotridecanoic acid ethyl ester other side products are also formed in step (ii), which leads to reduction in the yield.

Another drawback of this process is that step (iv) involves heterogeneous phase reaction and requires repetition of reduction three times for the completion of the reaction.

Yet another drawback of this process is that step (iv) involves the use of zinc amalgam, which leads to toxic effluent; thus the process is not environmental friendly.

Still another drawback of this process is that the quantity of effluent from each step of the process is very high which poses environmental hazards.

Still another drawback of this process is that in step (i), platinum black is used for the hydrogenation. Therefore, the process is also not cost-effective.

OBJECTS OF THE INVENTION n-Heneicosane is an oviposition attractant pheromone of the dengue transmitting mosquito, *Aedes aegypti* and hence is important component in attracticide formulations used for mosquito breeding. Also, n-heneicosane finds application in analytical chemistry, lubricant formulations, etc. It is indigenously not available in India. Therefore, there is a need to develop a simple and cost effective method for the preparation and process development of n-heneicosane, which can be up-scaled to manufacturing process and overcome the disadvantages/drawbacks of the processes known in the art.

Accordingly, it is an important object of the present invention to provide a new simple and novel method for the preparation of n-heneicosane by using indigenously available raw materials.

Another object of the present invention is to provide an environment-friendly process without using any hazardous chemicals.

Another object of the present invention is to provide a simple process for the preparation of n-heneicosane by reducing number of steps and energy conservative.

Further object of the present invention is to provide a new process for the preparation of n-heneicosane, which involves the use indigenously available chemicals to make the complete process cost effective.

Still another object of the present invention is to provide a new process for the preparation of n-heneicosane, which does not require the use of any flammable moisture-sensitive reagents.

Yet another object of the present invention is to provide a new process for the preparation of n-heneicosane, which gives the product of high purity and in quantitative yield.

Still another object of the present invention is to provide a new process for the preparation of n-heneicosane, which can easily be up-scaled.

Still another object of the present invention is to provide a new process for the preparation of n-heneicosane in which effluent load is minimum.

SUMMARY OF INVENTION

According to the present invention, a new process has been provided for the preparation of n-heneicosane. The process involves the following two steps:
  (i) preparation of 2-heneicosanone by the reaction of 2,4-propanedione with 1-bromooctadecane in absolute ethanol using 18-crown-6 as catalyst.
  (ii) preparation of n-heneicosane by the reduction of 2-heneicosanone using hydrazine hydrate and potassium hydroxide in diethylene glycol.

The overall yield and purity of n-heneicosane obtained are >95% and >99% respectively. The melting point is 41° C. (reported mp 39-42° C.). The process is simple, environment and is eco-friendly.

DETAILED DESCRIPTION

The present invention provides a process for the preparation of n-heneicosane which comprises:

(a) reacting 2,4-alkaneanedione with 1-bromooctadecane in absolute ethanol in the presence of 18-crown-6 as catalyst to produce 2-heneicosanone; and (b) reducing said 2-heneicosanone using hydrazine hydrate and potassium hydroxide in ethylene glycol to obtain n-heneicosane.

In a preferred feature, said 2,4-alkaneanedione is selected from 2,4-propanedione and 2,4-pentanedione.

In a preferred feature, said reaction of 2,4-alkaneanedione with 1-bromooctadecane in absolute ethanol is carried out in the presence of anhydrous potassium carbonate.

In a preferred feature, the amount said 2,4-alkanedione is 5 to 9 wt %, preferably, 7 to 8 wt %, the amount of said 1-bromooctadecane is 45 to 55 wt %, preferably 48 to 52 wt %, the amount of said 18-crown_6 is 0.005 to 0.009 wt %, preferably, 0.006 to 0.008 wt %, the amount of said anhydrous potassium carbonate is 10 to 15 wt %, preferably 11 to 12% and the amount of said absolute ethanol is 20 to 40 wt %, preferably 28 to 32 wt %.

In a preferred feature, in step (a), the reactants are refluxed at a temperature of 80-100° C. preferably 85-95° C. with continuous stirring for 24-42 hrs preferably, 30-36 hrs.

In a preferred feature, said ethylene glycol is selected from diethylene glycol and triethylene glycol.

In a preferred feature, said step (b) is carried out by refluxing 2-heneicosanone obtained in step (a) with a mixture of 8 to 15 wt %, preferably, 10 to 12 wt % of hydrazine hydrate, 10 to 15 wt %, preferably, 11 to 13 wt % of potassium hydroxide pellets and 55 to 70 wt %, preferably, 60 to 65 wt % (wt %) diethylene glycol or triethylene glycol.

In a preferred feature, said refluxing in step (b) is carried out at 90-130° C. preferably 110-120° C. with continuous stirring for 4-8 hrs, preferably 6-8 hrs, followed by removal of water and excess hydrazine from the mixture by distillation and further refluxing of the mixture at elevated temperature of 200-230° C. preferably 210-220° C. for 8-16 hrs preferably 11-13 hrs.

The preferred embodiments of the present invention will now be illustrated with the following non-limiting examples:

EXAMPLE 1

To a 2 L two-necked round bottom flask equipped with water condenser, calcium chloride guard tube and mechanical stirrer, 5-9% (wt %) of 2,4-pentanedione preferably 7-8% (wt %), 45-55% (wt %) of 1-bromooctadecane preferably 48-52% (wt %), 0.005 to 0.009% (wt %) of 18-crown-6 preferably 0.006-0.008% (wt %), anhydrous potassium carbonate 10-15% (wt %) preferably 11-12% (wt %) and absolute ethanol 20-40% (wt %) preferably 28-32% (wt %) were added with stirring. The mixture was refluxed at 80-100° C. preferably 85-95° C. with the above 2-heneicosanone was taken in a 3 L two necked flask equipped with water condenser, calcium chloride guard tube and mechanical stirrer. To this, 300 ml of hydrazine hydrate, 325 g of potassium hydroxide pellets and 1500 ml of diethylene glycol were added with stirring. The mixture was refluxed at 110° C. with continuous stirring for 6 hrs. Water and excess hydrazine from the mixture were removed by distillation and the temperature was elevated slowly to 210° C. for 11 hrs. After this, the reaction mixture was cooled to ambient temperature (25° C.) and treated with 1500 ml of water. The n-heneicosane separated by extraction with dichloromethane followed by evaporation. The crude n-heneicosane was purified by distillation (BP 129° C. at 0.05 mm Hg pressure) followed by re-crystallisation from acetone. The over all yield was >95% (282 g) and melting point was 41-42° C.

EXAMPLE 2

To a 2 L two-necked round bottom flask equipped with water condenser, calcium chloride guard tube and mechanical stirrer, 100 g of 2,4-pentanedione, 600 g of 1-bromooctadecane, 10 g of 18-crown-6, anhydrous potassium carbonate 125 g and 550 ml of absolute ethanol were added with stirring. The mixture was refluxed at 95° C. with continuous stirring for 24 hrs, after refluxing at the said temperature, the mixture was cooled to ambient temperature (25° C.), 550 ml of water was added to it and the 2-heneicosanone was extracted with dichloromethane from the mixture. On distillation of dichloromethane, 2-heneicosanone was obtained.

The above 2-heneicosanone was taken in a 3 L two-necked flask equipped with water condenser, calcium chloride guard tube and the mechanical stirrer. To this, 330 ml of hydrazine hydrate, 350 g of potassium hydroxide pellets and 1600 ml of triethylene glycol were added with stirring. The mixture was refluxed at 120° C. with continuous stirring for 8 hrs. Water and excess hydrazine from the mixture were removed by distillation and the temperature was elevated slowly to 220° C. for 12 hrs. Thereafter, the reaction mixture was cooled to ambient temperature (25° C.) and treated with 1600 ml of water. The n-heneicosane separated by extraction with dichloromethane followed by evaporation. The crude n-heneicosane was purified by distillation (BP 129° C. at 0.05 mm Hg pressure) followed by re-crystallisation from acetone. The over all yield was >95% (282 g) and melting point was 41-42° C.

EXAMPLE 3

To a 2 L two-necked round bottom flask equipped with water condenser, calcium chloride guard tube and mechanical stirrer, 70 g of 2,4-pentanedione, 650 g of 1-bromooctadecane, 8 g of 18-crown-6, anhydrous potassium carbonate 140 g and 600 ml of absolute ethanol were added with stirring. The mixture was refluxed at 90° C. with continuous stirring for 30 hrs; after refluxing at the said temperature, the mixture cooled to ambient temperature (25° C.), 600 ml of water was added to it and the 2-heneicosanone was extracted with dichloromethane from the mixture. On distillation of dichloromethane, 2-heneicosanone was obtained.

The above 2-heneicosanone was taken in a 3 L two-necked flask equipped with water condenser, calcium chloride guard tube and mechanical stirrer. To this, 280 ml of hydrazine hydrate, 300 g of potassium hydroxide pellets and 1500 ml of diethylene glycol were added with stirring. The mixture was refluxed at 110° C. with continuous stirring for 6 hrs. Water and excess hydrazine from the mixture were removed by distillation and the temperature was elevated slowly to 210° C. for 11 hrs. After this, the reaction mixture was cooled to ambient temperature (25° C.) and treated with 1500 ml of water. The n-heneicosane separated by extraction with dichloromethane followed by evaporation. The crude n-heneicosane was purified by distillation (BP 129° C. at 0.05 mm Hg pressure) followed by re-crystallisation from acetone. The over all yield was >95% (282 g) and melting point was 41-42° C.

We claim:

1. A process for the preparation of n-heneicosane which comprises:
   (a) reacting 2,4-alkaneanedione with 1-bromooctadecane in absolute ethanol in the presence of 18-crown-6 as catalyst to produce 2-heneicosanone; and
   (b) reducing said 2-heneicosanone using hydrazine hydrate and potassium hydroxide in ethylene glycol to obtain n-heneicosane.

2. The process as claimed in claim 1 wherein said 2,4-alkaneanedione is selected from the group consisting of 2,4-propanedione and 2,4-pentanedione.

3. The process as claimed in claim 1, wherein said reaction of 2,4-alkaneanedione with 1-bromooctadecane in absolute ethanol is carried out in the presence of anhydrous potassium carbonate.

4. The process as claimed in claim 3, wherein the amount said 2,4-alkanedione is 5 to 9 wt %, the amount of said 1-bromooctadecane is 45 to 55 wt %, the amount of said 18-crown 6 is 0.005 to 0.009 wt %, the amount of said anhydrous potassium carbonate is 10 to 15 wt %, and the amount of said absolute ethanol is 20 to 40 wt %.

5. The process as claimed in claim 1, wherein in step (a), the reactants are refluxed at a temperature of 80-100° C. with continuous stirring for 24-42 hrs.

6. The process as claimed in claim 1, wherein said ethylene glycol is selected from the group consisting of diethylene glycol and triethylene glycol.

7. The process as claimed in claim 1, wherein said step (b) is carried out by refluxing 2-heneicosanone obtained in step (a) with a mixture of 8 to 15 wt % of hydrazine hydrate, 10 to 15 wt % of potassium hydroxide pellets and 55 to 70 wt % of diethylene glycol or triethylene glycol.

8. The process as claimed in claim 7 wherein said refluxing instep (b) is carried out at 90-130° C. with continuous stirring for 4-8 hrs, followed by removal of water and excess hydrazine from the mixture by distillation and further refluxing of the mixture at elevated temperature of 200-230° C. for 8-16 hrs.

9. The process as claimed in claim 4, wherein the amount said 2,4-alkanedione is 7 to 8 wt %.

10. The process as claimed in claim 4, wherein the amount of said 1-bromooctadecane is 48 to 52 wt %.

11. The process as claimed in claim 4, wherein the amount of said 18-crown-6 is 0.006 to 0.008 wt %.

12. The process as claimed in claim 4, wherein the amount of said anhydrous potassium carbonate is 11 to 12 wt %.

13. The process as claimed in claim 4, wherein the amount of said absolute ethanol is 28 to 32 wt %.

14. The process as claimed in claim 5, wherein in step (a), the reactants are refluxed at a temperature of 85-95° C.

15. The process as claimed in claim 5, wherein in step (a), the reactants are refluxed with continuous stirring for 30-36 hrs.

16. The process as claimed in claim 7, wherein the amount of said hydrazine hydrate in the mixture is 10 to 12 wt %.

17. The process as claimed in claim 7, wherein the amount of said potassium hydroxide in the mixture is 11 to 13 wt %.

18. The process as claimed in claim 7, wherein the amount of said diethylene glycol or triethylene glycol in the mixture is 60 to 65 wt %.

19. The process as claimed in claim 8, wherein said refluxing in step (b) is carried out at 110-120° C.

20. The process as claimed in claim 8, wherein said refluxing in step (b) is carried out with continuous stirring for 6-8 hrs.

21. The process as claimed in claim 8, wherein the further refluxing of the mixture is carried out at temperature of 210-220° C.

22. The process as claimed in claim 8, wherein the further refluxing of the mixture is carried out for 11-13 hrs.

* * * * *